United States Patent [19]
Schmittmann et al.

[11] Patent Number: 6,022,545
[45] Date of Patent: *Feb. 8, 2000

[54] USAGE OF PATHOGEN-KILLING FOAMS

[75] Inventors: H. B. Schmittmann, Velbert; J. Dietrich, Monheim, both of Germany

[73] Assignee: Nouveau Technologies, Inc., Tequesta, Fla.

[*] Notice: This patent issued on a continued prosecution application filed under 37 CFR 1.53(d), and is subject to the twenty year patent term provisions of 35 U.S.C. 154(a)(2).

[21] Appl. No.: 08/668,407

[22] Filed: Jun. 21, 1996

[51] Int. Cl.$^7$ .......................... A01N 65/00; A01N 59/20; A01N 43/04
[52] U.S. Cl. .................. 424/195.1; 424/638; 514/31; 514/33; 514/34
[58] Field of Search .................... 424/638, 195.1; 514/31, 33, 34

[56] References Cited

PUBLICATIONS

Szalontai et al 87 CA: 96715g 1977.
Szalontai et al 86 CA: 101395p 1977.
Lalitha et al 115 CA: 154850g 1991.
Okunji et al 114 CA: 244239y 1991.
Mar. Ind. 10th Ed 1985 #8218,2645, 1995.

*Primary Examiner*—Russell Travers
*Attorney, Agent, or Firm*—McHale & Slavin

[57] ABSTRACT

This invention describes the effect of a means to prevent the sexual transmission of infectious pathogens of the vaginal and uterine wall in women, farm animals and pets. This discovery concerns a means to disrupt the sexual transmission of infectious pathogens which attack the cavity living of the vagina and uterus of women, farm animals and pets which consists of a foam that prevents the docking of pathogens to the cavity lining and which acts as a pathogen-killing substance.

28 Claims, No Drawings

USAGE OF PATHOGEN-KILLING FOAMS

FIELD OF THE INVENTION

This discovery concerns a foam to disrupt the sexual transmission of infectious pathogens like viruses and/or bacteria, which especially attack humans as well as farm animals and pets.

BACKGROUND OF THE INVENTION

The transmission mechanism of pathogenic agents through sexual contact are readily recognized.

As is well-known, a global danger to humanity has resulted from the appearance of HIV infectious disease AIDS in recent history. Considerable expenditures have been dedicated to the research for medicines to combat this disease. In order to prevent the possible transmission of pathogens during sexual contact, condoms are used which should automatically create a barrier to hinder any intrusion of viruses and/or bacteria into the cavity lining of the vagina and uterus. However, a condom's preventive effect can be lost due to undiscovered defects which can never be ruled out. In addition, a condom reduces subjective sensitivity and thereby further interferes with sexual intercourse.

EP-A 088 of 394 describes a foam-creating suppository which contains saponin and furthermore could contain antibacterial, anti-inflammatory and anti-mykotic substances.

U.S. Pat. No. 3,886,272 describes the spermicide effect of the saponin and its effect on the cavity lining.

Ref. Rao G. S., Cochran K. W., J. Pharm. Sci. 63 (1974) 471–473, which describes the anti-viral potency of the saponins.

Ref. G. Wulff, German Pharmacist-Newspaper 108 (1068) 797–808, which describes the antibiotic potency of the saponins.

SUMMARY OF THE INVENTION

This invention describes the effect of a pathogen-killing foam which simply and easily can prevent the infection of the vaginal and uterine wall in women, farm animals and pets.

This goal will be achieved as described in claim no. 1.

The sub-claim lists advantageous details of this invention.

The object of this invention is the usage of a foam, which can prove to have pathogen-killing properties and may contain additional substances that prevent by means of an adhesion block, the docking of pathogens to the cavity lining. The foam bubbles which come into contact with the cavity lining will most probably burst and thereby create a closed filmy covering on the surface of the lining.

DETAILED DESCRIPTION OF THE PREFERRED EMBODIMENT

The foam, in particular, a saponin foam, will be composed of air or another gas encapsulated inside bubbles which superficially will hold together and whose surface consists of a saponin/water mixture.

In addition to the foam substance this invention can prove to have pathogen-killing properties. This would be a unique advantage if the foam substance naturally works as a pathogen killer, which is possible when using saponin for example.

A surprising effect is that the saponin foam or the surface of the saponin bubbles will completely cover and protect the cavity lining so that the lining is shielded from contact without outside pathogens. This is because the saponin foam or, more exactly, the bubbles' surface would contact the entire cavity lining and practically eliminate, by means of an adhesion block, the docking of pathogens to the cavity lining. Another surprising aspect of this method is that saponin foam or its surface substance adheres to and remains affixed to the cavity lining. The foam's adhesive properties, therefore, provide a protection which is long-term. An even further surprising property of this foam is that its saponin containing surface substance can extensively kill pathogens, especially viruses, but also bacteria.

Preferably, the saponin foam which is to be used or produced in loco should have bubbles with a diameter of 0.001 mm to 1 mm with a saponin content in the surface of 0.01 to 2% by weight.

A special advantage of the saponin foam is that it can be mixed or supplemented with additional, familiar pathogen-killing substances—for example with fungicides, anti-bacterial and anti-viral agents as well as active substances which fight pathogenic protozoa. These agents can also function as carrier substances. These additional chemical components will become homogenized in the bubbles' surface membrane where they will render their additive effects.

This newly-invented means of prevention against pathogenic protozoa by means of the disinfective effect already ensured by the saponin content of its foam. However, the foam's disinfective properties can be improved deliberately by adding additional chemical agents. The transmission of pathogenic microbes, protozoa, and viruses to the cavity linings under discussion will be disrupted by the use of an adhesion blockage and/or killing-off and/or destruction and/or immobilization of the infection-causing factors. Especially in the so-called cavities, this prevention generates a potent prevention against the transmission of HIV infection. This potent prevention is attained without generating any noticeable, additional obstructions and/or hindrances.

In proper doses, this new use of foams will not adversely effect the cavities' superficial mucous membrane. The foam bubbles which come into contact with the cavity lining will most probably burst, and thereby create a closed filmy covering on the surface of the lining. This covering guarantees a total shielding of the surface or tissues. What the result of the killing-off effect of the saponin substance has on, for example, HIV has not yet been researched. However, the important factor is that the killing-of or elimination of any harmful effects is complete in just a few minutes. This occurs in a time frame during which the foam has not yet decomposed or the totally encapsulating foam layer shows any gaps. In accordance with the invention, the destruction of pathogens transpires faster than the possibility of an adhesion which could precede the penetration of the mucous membrane of the cavity's body.

The saponin foam, as most mentioned, serves as a so-called "carrier" for antibacterial, anti-viral, or similar pathogen-killing compounds, or even other general disinfectant. For example, copper sulfate pentahydrate, preferably in a relationship of 1 to 50,000 to 1 to 70,000 or for example 1 to 60,000—could be added as the watery saponin solution. Copper sulfate pentahydrate is well known as a sterilizing agent, and it supports and accelerates the complete killing-off of pathogens. In addition to this, any well-known compound—like chamomile extract—can be added to the solution to suppress any possible irritation of the mucous membrane which might show up.

The use of these substances can be applied either by introduction into the cavities of a foamy, watery saponin solution or through the use of a substance in tablet or power form, or the like which, once introduced, will produce form with the fluids already found there. This will occur primarily through the production of carbon dioxide. Removal of the substance from the cavity can be achieved by simple cleaning with, for example, water.

This invention suggests the usage of a foam agent, with which the walls of the cavities—as described—can be protected temporarily with a closed layer of foam so that a log-on of pathogens is not possible. In addition, this foam will quickly have a disinfective effect either by itself or in conjunction with other given additives. The homogenous distribution and entire protection of the cavity walls is achieved, according to the invention, in the form of this foam. A further advantage of a foam is that a relatively large surface space will be covered by a relatively large amount of active foam substance which causes no reduction in sensitivity.

The use of saponin as the foam substance has the synergistic effect of the homogenous protection of the mucous as well as the foam's disinfective properties.

EXAMPLES

1). To produce a usable foam in accordance with the invention, 0.5 kg quilliajan saponin DAB9 and 0.0002 kg copper sulfate pentahydrate are dissolved in 99.5 liters of 1% chamomile tea. This solution is then foamed according to familiar procedures and filled into spray cans.

2). To produce a foam tablet, the following is mixed:

1 g natrium bicarbonate with 0.03 g hydrophile pyrogene aerosol, 0.07 quilliajan saponin DAB, 0,001 g copper sulfate, 1.4 g citric acid.
This mixture is then pressed into a tablet.

It is to be understood that while we have described certain forms of our invention, it is not to be limited to the specific form or arrangement herein described. It will be apparent to those skilled in the art that various changes may be made without departing from the scope of the invention and the invention is not to be considered limited to what is described in the specification.

What is claimed is:

1. A method to prevent adhesion of pathogens to the lining of a cavity within a human being or animal comprising:
   insertion of a bubble containing saponin foam material within said cavity, said saponin content being about 0.01 to 2% of said foam material's total weight, said foam further including an additional and distinct antimicrobial agent; and
   production of a closed filmy covering on the lining of said cavity, said closed filmy covering being formed upon contact and bursting of said foam bubbles on the surface of the cavity lining.

2. The method according to claim 1 wherein said foam material is further characterized as containing foam bubbles having a diameter of about 0.001 to 1 mm.

3. The method according to claim 1 further including the step of adding a sterilizing agent characterized as copper sulfate pentahydrate to the foam material.

4. The method according to claim 3 wherein said copper sulfate pentahydrate has a ratio of about 1 to 60,000 in relation to said foam.

5. The method according to claim 1 including the step of adding a mucous membrane irritation reduction agent to the foam material.

6. The method according to claim 5 wherein said reduction agent is characterized as a chamomile extract.

7. A method to prevent adhesion of pathogens to the lining of a cavity within a human being or animal comprising:
   insertion of a saponin foam-building substance within said cavity; said saponin content being about 0.01 to 2% of said foam-building substance's total weight, said foam-buildinq substance further including an Additional and distinct antimicrobial agent; and
   admixture of said foam-building substance with liquids in said cavity to form a bubble containing foam;
   wherein contact and bursting of said foam bubbles which come into contact with the lining of said cavity create a closed filmy covering on the surface of the lining.

8. The method according to claim 7 wherein said foam building substance is further characterized as containing foam bubbles having a diameter of about 0.001 to 1 mm.

9. The method according to claim 7 further including the step of adding a sterilizing agent characterized as copper sulfate pentahydrate to the foam building substance.

10. The method according to claim 9 wherein said copper sulfate pentahydrate has a ratio of about 1 to 60,000 in relation to said foam.

11. The method according to claim 7 including the step of adding a mucous membrane irritation reduction agent to the foam building substance.

12. The method according to claim 10 wherein said reduction agent is characterized as a chamomile extract.

13. A method for inhibiting the transmission of sexually transmitted diseases caused by viral or bacterial pathogens by preventing adhesion of said pathogens to the vaginal cavity comprising:
   inserting within the vaginal cavity an effective amount of a bubble-containing saponin foam including an additional and distinct antimicrobial agent therein; and
   allowing said foam to mix with liquid present in the cavity so as to form a closed filmy covering which covers both the vaginal and uterine cavity lining;
   whereby an adhesive covering which provides long-term protection forms upon said cavity linings and provides an effective block against the docking of pathogens to the cavity lining.

14. A method for inhibiting the transmission of HIV by preventing adhesion of said pathogens to the vaginal cavity comprising:
   inserting within the vaginal cavity an effective amount of a bubble-containing saponin foam including an additional and distinct antimicrobial agent therein; and
   allowing said foam to mix with liquid present in the cavity so as to form a closed filmy covering which covers both the vaginal and uterine cavity lining;
   whereby an adhesive covering which provides long-term protection forms upon said cavity linings and provides an effective block against the docking of pathogens to the cavity lining.

15. The method according to claim 13 wherein said saponin content is equal to about 0.01 to 2% of said foam material's total weight.

16. The method according to claim 14 wherein said saponin content is equal to about 0.01 to 2% of said foam material's total weight.

17. The method according to claim 13 wherein the step of inserting comprises the insertion of a foam producing substance in tablet or powder form so as to produce a foam with the fluids already found in the vaginal cavity.

18. The method according to claim 14 wherein the step of inserting comprises the insertion of a foam producing substance in tablet or powder form so as to produce a foam with the fluids already found in the vaginal cavity.

19. The method according to claim 13 wherein said foam material is further characterized as containing foam bubbles having a diameter of about 0.001 to 1 mm.

20. The method according to claim 14 wherein said foam material is further characterized as containing foam bubbles having a diameter of about 0.001 to 1 mm.

21. The method according to claim 13 further including the step of adding a sterilizing agent characterized as copper sulfate pentahydrate to the foam material.

22. The method according to claim 21 wherein said copper sulfate pentahydrate has a ratio of about 1 to 60,000 in relation to said foam.

23. The method according to claim 14 further including the step of adding a sterilizing agent characterized as copper sulfate pentahydrate to the foam material.

24. The method according to claim 23 wherein said copper sulfate pentahydrate has a ratio of about 1 to 60,000 in relation to said foam.

25. The method according to claim 13 including the step of adding a mucous membrane irritation reduction agent to the foam material.

26. The method according to claim 25 wherein said reduction agent is characterized as a chamomile extract.

27. The method according to claim 14 including the step of adding a mucous membrane irritation reduction agent to the foam material.

28. The method according to claim 27 wherein said reduction agent is characterized as a chamomile extract.

* * * * *